(12) United States Patent
Blin et al.

(10) Patent No.: US 7,919,105 B2
(45) Date of Patent: *Apr. 5, 2011

(54) COSMETIC COMPOSITION WITH CONTINUOUS LIPOPHILIC PHASE CONTAINING FLAT FIBERS

(75) Inventors: Xavier Blin, Paris (FR); Nathalie Jager Lezer, Bourg-la-Reine (FR)

(73) Assignee: L'Oreal S.A., Paris (FR)

( * ) Notice: Subject to any disclaimer, the term of this patent is extended or adjusted under 35 U.S.C. 154(b) by 952 days.

This patent is subject to a terminal disclaimer.

(21) Appl. No.: 10/432,217

(22) PCT Filed: Nov. 22, 2001

(86) PCT No.: PCT/FR01/03694
§ 371 (c)(1),
(2), (4) Date: Aug. 1, 2003

(87) PCT Pub. No.: WO02/41852
PCT Pub. Date: May 30, 2002

(65) Prior Publication Data
US 2004/0076649 A1 Apr. 22, 2004

(30) Foreign Application Priority Data

Nov. 23, 2000 (FR) .................................. 00 15134

(51) Int. Cl.
*A61K 8/02* (2006.01)
(52) U.S. Cl. .................................. 424/401; 424/400
(58) Field of Classification Search .................. None
See application file for complete search history.

(56) References Cited

U.S. PATENT DOCUMENTS

| 4,659,562 | A | * | 4/1987 | Arraudeau et al. ............. 424/63 |
|---|---|---|---|---|
| 4,820,510 | A | | 4/1989 | Arraudeau et al. |
| 5,472,798 | A | | 12/1995 | Kumazawa et al. |
| 5,498,407 | A | | 3/1996 | Atlas |
| 5,750,723 | A | | 5/1998 | Eldin et al. |
| 5,945,095 | A | | 8/1999 | Mougin et al. |
| 6,001,338 | A | * | 12/1999 | Mondet .......................... 424/61 |
| 6,048,918 | A | | 4/2000 | Eldin et al. |
| 6,254,877 | B1 | | 7/2001 | De La Poterie et al. |
| 6,491,931 | B1 | * | 12/2002 | Collin ........................... 424/401 |
| 6,689,345 | B2 | * | 2/2004 | Jager Lezer .................... 424/64 |
| 6,726,917 | B2 | * | 4/2004 | Kanji et al. ................... 424/401 |

FOREIGN PATENT DOCUMENTS

| EP | 0 106 762 | 4/1984 |
|---|---|---|
| EP | 0 542 669 | 5/1993 |
| EP | 0 686 858 | 12/1995 |
| EP | 0 749 746 | 12/1996 |
| EP | 0 787 730 | 8/1997 |
| EP | 0 787 731 | 8/1997 |
| EP | 0 921 217 | 6/1999 |
| EP | 0 923 928 | 6/1999 |
| EP | 0 930 060 | 7/1999 |
| FR | 1 529 329 | 6/1968 |
| FR | 2 477 173 | 9/1981 |
| GB | 2 070 622 | 9/1981 |
| JP | 57-158714 | 9/1982 |
| JP | 62-164731 | 7/1987 |
| JP | 7-196440 | 8/1995 |
| JP | 2000-319131 | 11/2000 |
| WO | WO 96/08537 | 3/1996 |

OTHER PUBLICATIONS

English language Derwent Abstract of EP 0 923 928, Jun. 23, 1999.
English language Derwent Abstract of JP 57-158714, Sep. 30, 1982.
English language Derwent Abstract of JP 62-164731, Jul. 21, 1987.
English language Derwent Abstract of JP 7-196440, Aug. 1, 1995.

* cited by examiner

*Primary Examiner* — Robert A Wax
*Assistant Examiner* — Hasan S Ahmed
(74) *Attorney, Agent, or Firm* — Finnegan, Henderson, Farabow, Garrett & Dunner LLP

(57) ABSTRACT

The present invention relates to a cosmetic composition with a lipophilic continuous phase, in particular a make-up composition, containing flat fibers.

The subject of the invention is also a make-up kit containing a first composition comprising a coloring matter and a second composition comprising a lipophilic continuous phase and flat fibers.

The subject of the invention is also a cosmetic method or a method for the care of keratinous materials.

185 Claims, No Drawings

COSMETIC COMPOSITION WITH CONTINUOUS LIPOPHILIC PHASE CONTAINING FLAT FIBERS

The present invention relates to a cosmetic composition containing flat fibres, and more especially to a make-up composition for the skin both of the face and of the human body, of the lips and of superficial body growths such as the nails, the eyelashes, the eyebrows or the hair.

The composition according to the invention may be a make-up composition such as products for the complexion (foundations which are coloured or otherwise), make-up for the cheeks or eye shadows, lip products which are coloured or otherwise, concealers, blushers, mascaras which are coloured or otherwise, eyeliners, make-up products for the eyebrows, lip or eye pencils, nail products which are coloured or otherwise, make-up products for the body, make-up products for the hair (hair mascara or lacquer), or a care composition for the skin such as the compositions intended for concealing skin imperfections. The composition may be used as it is for application to the keratinous materials or may be applied over a make-up already deposited on the keratinous materials, for example for modifying the make-up (the composition is applied as a top product commonly called top coat).

The make-up composition may also be applied over make-up accessories (support) such as false nails, false eyelashes, postiches, wigs or over pastilles or patches adhering to the skin or the lips (of the beauty-spot type).

It is known to use fibres in make-up products, in particular for their lengthening effects in mascaras (see JP-A-57/158714), their moisturizing properties in lipsticks (see the document U.S. Pat. No. 5,498,407), for improving the contours of lipsticks on the edges of the lips (see the document EP-A-0106762) or for repairing broken nails (see FR-A-1529329) or in care products for the skin for their velvety feel (JP-A-7/196440). Unfortunately, it is very difficult to disperse fibres in compositions homogeneously and without forming lumps, which, in a cosmetic composition and in particular in a make-up composition, generally gives a deposit on the keratinous materials, in particular a make-up, which is not uniform and not very aesthetic, having a contour which is not very sharp. Furthermore, the lumps of fibres due to the poor dispersion of the fibres modify the visual appearance of the composition.

In addition, this difficulty of dispersion leads to compositions having cosmetic properties which are not constant and not very reproducible, and generally causes problems of industrial manufacture and high costs of manufacture.

The aim of the present invention is therefore to provide a topical composition not exhibiting the above disadvantages and comprising fibres which are homogeneously distributed.

The inventors have discovered that flat fibres, that is to say fibres whose section has a flattened shape, are very easily incorporated into the cosmetic compositions and become homogeneously distributed in the composition.

The incorporation of flat fibres into the composition can be done very easily, both in the cold state and in the hot state, without losing the cosmetic properties of the composition. In particular, the good homogeneity of the fibres in the composition does not change the appearance of the product. It is possible to incorporate large amounts of flat fibres into the composition without modifying the visual appearance of the composition.

The composition applied to the keratinous materials forms a deposit exhibiting a velvety feel to the touch due to the homogeneous dispersion of the flat fibres in the composition and in the deposit formed after the application. The composition therefore provides a different feel to the smooth, crackled or granular feel, thus satisfying consumers seeking novelty.

In addition, the flat fibres provide properties of mechanical strengthening of the composition and of the deposit formed after application to the keratinous materials, in particular when the deposit comprises a film-forming polymer. In particular, the composition forms a deposit exhibiting good properties of mechanical resistance: the deposit is very resistant to rubbing, to shock and to scratching. The deposit is also very resistant to water (in particular during bathing or showering), rain, tears, sweat and sebum. The flat fibres thus provide a better retention of the deposit on the keratinous materials.

The composition comprising flat fibres applied to the skin makes it possible to obtain good concealing of skin imperfections.

The flat fibres also confer a bright visual effect. When they are formulated in a transparent or translucent carrier, the composition may be applied as a top coat over a make-up already deposited on the keratinous materials so as to thus modify the appearance of the make-up.

In addition, the particular colour effect of the make-up is clearly visible when the composition is applied to dark skins such as ethnic skins.

More precisely, the subject of the invention is a composition for topical application with a lipophilic continuous phase, and more especially a make-up cosmetic composition with a lipophilic continuous phase, containing flat fibres.

The subject of the invention is also a cosmetic method for applying make-up to or caring for keratinous materials comprising the application, to the keratinous materials, of a composition as defined above.

The subject of the invention is also the use of flat fibres in a cosmetic composition comprising a lipophilic continuous phase for mechanically strengthening the deposit obtained after the application of the said composition to keratinous materials, and/or the said composition.

The subject of the invention is also a cosmetic method for applying make-up to the keratinous materials comprising the application to the keratinous materials of a first layer, also called base layer, of a first cosmetic composition comprising, in a cosmetically acceptable medium, at least one colouring matter, then the application, to at least a portion of the said first layer, of a second layer of a second cosmetic composition comprising, in a cosmetically acceptable lipophilic continuous medium, flat fibres, the first composition not comprising flat fibres as present in the second composition.

The subject of the invention is also a make-up kit comprising:
  a first composition comprising at least one colouring matter in a cosmetically acceptable medium, and
  a second composition comprising flat fibres in a cosmetically acceptable lipophilic continuous medium, the first composition not comprising flat fibres as present in the second composition, the first and second compositions being packaged in separate containers.

The subject of the invention is also a support to which make-up has been applied, such as the make-up accessories cited above, comprising a make-up which is capable of being obtained according to the make-up application method as defined above and applied to the said support.

The expression "fibre" should be understood to mean an object having a length L and a diameter D such that L is much greater than D, D being the diameter of the circle in which the section of the fibre is inscribed. In particular, the ratio L/D (or shape factor) is chosen from the range going from 1.2 to 2 500, preferably from 1.5 to 500, and better still from 1.6 to 150.

The expression "flat fibre" is understood to mean a fibre whose cross section (section perpendicular to the axis of the direction of the length of the fibre) has a longer length L1 and a shorter length L2 (L2 corresponds to the thickness of the fibre) such that L1/L2 (ratio L1/L2 is also called flattening factor) is greater than or equal to 4, preferably greater than 7. In particular, L1/L2 ranges from 4 to 15, preferably from 6 to 12, and better still from 7 to 10. Thus, the cross section of the fibre has a flat shape. Advantageously, the longer length L1 and the shorter length L2 define axes X1, X2, respectively, such that the axis X1 is substantially perpendicular to the axis X2. The longer length L1 corresponds to the diameter D of the fibre as mentioned above. Thus, the flat fibres may be provided in the form of ribbons or tagliatelle.

The flat fibres may in particular have a cross section which is substantially rectangular, ovoid or ellipsoid.

The fibres which can be used in the composition of the invention may be fibres of synthetic or organic origin, and more particularly fibres of synthetic polymer. They may be short or long, unitary (or monofilament) or organized, for example plaited (or multifilament), hollow or solid, preferably solid. When the fibres are multifilament fibres, each filament may be of a different chemical composition and may have a different colour: multifilament fibres having different colours are thus obtained. In particular, their ends are blunt and/or smooth to avoid injury. Advantageously, the flat fibres are insoluble in water.

The flat fibre may be twisted along the axis of the length L of the fibre. When the flat fibre is not twisted, it exhibits a colour in a certain angle of view; outside this angle, the fibre is transparent or white in colour. The twisted flat fibre, for its part, exhibits a colour regardless of the angle of observation.

In particular, the fibres have a length ranging from 1 µm to 10 mm, preferably from 0.1 mm to 5 mm and better still from 0.3 mm to 3.5 mm. Their section (flat section) may be included in a circle having a diameter ranging from 2 nm to 500 µm, preferably ranging from 100 nm to 100 µm and better still from 1 µm to 70 µm. The weight or titre of the fibres is often given in denier or decitex and represents the weight, in grams, for 9 km of thread. Preferably, the fibres according to the invention have a titre chosen from the range going from 0.15 to 30 denier and better still from 0.18 to 18 denier.

The fibres may be those used in the manufacture of textiles and in particular of rayon fibre, polyamide (Nylon®) fibre, viscose fibre, acetate fibre, in particular rayon acetate fibre, poly(p-phenylene-terephthalamide) (or aramide) fibre, in particular Kevlar® fibre, acrylic polymer fibre, in particular polymethyl methacrylate fibre or poly-2-hydroxyethyl methacrylate fibre, polyolefin fibre and in particular polyethylene or polypropylene fibre, polytetrafluoroethylene fibre (such as Teflon®), polyvinyl or polyvinylidene chloride fibre, polyvinylidene fluoride fibre, polyvinyl alcohol fibre, polyacrylonitrile fibre, polyurethane fibre, polyester fibre such as polyethylene terephthalates and polyethylene naphthalates, and polycarbonate fibre.

Moreover, the fibres may be surface-treated or otherwise, or may be coated with a protective layer or otherwise.

The fibres which can be used in the composition according to the invention are preferably polyester, acrylic polymer and polyamide fibres.

According to a particular embodiment of the composition according to the invention, the flat fibres are fibres with a multilayer structure of polymer, the said layers being such that they allow the creation of a colour effect by inteferences of light rays, which diffract and diffuse differently according to the layers, Thus, such fibres may have colours which vary according to the angle of observation and the incidence of light, and may confer irridescent glints. Fibres with multilayer structure of polymers are in particular described in the documents EP-A-921217, EP-A-686858 and U.S. Pat. No. 5,472,798.

The multilayer structure may comprise at least two layers, each layer, independently or otherwise of the other layer(s), being made of at least one synthetic polymer.

The flat fibre may be formed of alternate individual layers of polymers having different refractive indices; each layer being in a plane (P) parallel to the direction of the principal axis of the fibre, in the direction of its length L. According to the thickness of each of the different layers, different colours are obtained. In general, the structure is composed of alternating layers of low refractive index and of high refractive index. Thus, in a cross section to the direction of the axis of the length L of the fibre, the fibre has a multilayer structure comprising alternate layers of at least a first polymer and a second polymer.

The multilayer part of the fibre may comprise at least 5 individual layers of polymer, in particular from 5 to 120, preferably at least 10 layers, in particular from 10 to 70 layers, and better still from 10 to 50 layers.

Each layer of the first and second polymers has respectively a thickness $d_1$, $d_2$ which may range, independently of each other, from 0.02 µm to 0.3 µm, and preferably from 0.05 µm to 0.15 µm.

Advantageously, the polymers present in the fibres advantageously have a refractive index ranging from 1.30 to 1.82 and better still ranging from 1.35 to 1.75. In particular, the first and second polymers have respectively a refractive index $n_1$ and $n_2$ such that $n_1/n_2$ ranges from 1.1 to 1.4.

Advantageously, $n_1$, $n_2$, $d_1$, $d_2$ satisfy the equation:

$$\lambda = 2(n_1 d_1 + n_2 d_2) = 2n_1[d_1 + d_2(n_2/n_1)]$$

in which $\lambda$ is the wavelength, expressed in µm, of the colour of the fibre formed by optical interference (wavelength of the peak of the reflection spectrum); $d_1$ and $d_2$ being expressed in µm.

The flat fibre with multilayer structure preferably has a reflection spectrum such that the width at half height of the spectrum $\lambda_{L=1/2}$ is in the range $0 < \lambda_{L=1/2} < 200$ nm.

The polymers constituting the fibres which are particularly preferred are polyesters such as polyethylene terephthalate, polyethylene naphthalate, polycarbonate; acrylic polymers such as polymethyl methacrylate; polyamides.

The polyethylene terephthalate may be obtained by polycondensation of terephthalic acid with ethylene glycol. It may contain from 0 to 30% by weight, preferably from 0 to 15% by weight, and better still from 0 to 10% by weight, relative to the total weight of the monomers, of other comonomers.

In particular, the polyethylene terephthalate may comprise from 0.3 to 10 mol %, and preferably from 0.5 to 5 mol %, of dicarboxylic acid monomer comprising a sulphonic acid group neutralized by a metal salt, relative to the total weight of the dicarboxylic acid monomer present in the polyethylene terephthalate.

The sulphonic acid group neutralized by a metal salt is a group of formula —$SO_3M$ in which M is a metal, preferably an alkali or alkaline-earth metal, and more particularly sodium, potassium or lithium.

As example of dicarboxylic acid monomer comprising a sulphonic acid group neutralized by a metal salt, there may be used the sodium salt of 5-sulphoisophthalic acid, the potassium salt of 5-sulphoisophthalic acid, the lithium salt of 5-sulphoisophthalic acid, and the methyl diesters thereof, sodium 3,5-di (β-hydroxyethoxycarbonyl) benzenesulphonate, potassium 3,5-di(β-hydroxyethoxycarbonyl)benzenesulphonate, lithium 3,5-di(β- hydroxyethoxycarbonyl)benzenesulphonate, sodium 4-sulphonate-2,6-naphthalic acid methyl diester, potassium 4-sulphonate-2,6-naphthalic acid methyl diester, lithium 4-sulphonate-2,6-naphthalic acid methyl diester, sodium 2,6-dicarboxynaphthalene-4-sulphonate, sodium 2,6-dicarboxynaphthalenel-sulphonate, 3-sulphonate-2,6-naphthalic acid methyl diester, sodium 4,8-disulphonate-2,6-naphthalic acid methyl diester, sodium 2,6-dicarboxynaphthalene-4,8-disulfonate, sodium 2,5-bis (hydroxyethoxy)benzenesulphonate, sodium sulphosuccinate, and mixtures thereof. Sodium 5-sulphoisophthalic acid methyl diester, the sodium salt of 5-sulphoisophthalic acid and sodium 3,5-di(β-hydroxyethoxycarbonyl)benzenesulphonate are preferably used.

The polyethylene naphthalate may be obtained by polycondensation of 2,6-naphthalic acid or of 2,7-naphthalic acid with ethylene glycol. The polyethylene naphthalate may therefore be a polyethylene-2,6-naphthalate or a polyethylene-2,7-naphthalate, preferably a polyethylene-2,6-naphthalate.

It may contain from 0.3 to 5 mol % of dicarboxylic acid monomer comprising a sulphonic acid group neutralized by a metal salt as defined above, relative to the total weight of the dicarboxylic acid monomer present in the polyethylene naphthalate.

Other comonomers such as an additional dicarboxylic acid, different from the dicarboxylic acids mentioned above, or an additional diol, different from polyethylene glycol, may be present in the polyethylene terephthalate or the polyethylene naphthalate.

The additional dicarboxylic acid may be chosen from the aromatic dicarboxylic acids such as isophthalic acid, biphenyldicarboxylic acid, 4,4'-dicarboxylic acid of diphenyl ether, 4,4'-dicarboxylic acid of diphenylmethane, 4,4'-dicarboxylic acid of diphenyl sulphone, 4,4'-dicarboxylic acid of 1,2-diphenoxyethane, 2,5-pyridinedicarboxylic acid, 2,6-naphthalenedicarboxylic acid, 2,7-naphthalenedicarboxylic acid, dicarboxylic acid of diphenyl ketone; aliphatic dicarboxylic acids such as malonic acid, succinic acid, adipic acid, azelaic acid, sebacic acid; alicyclic dicarboxylic acids such as dicarboxylic acid of decalin; hydroxycarboxylic acids such as β-hydroxyethoxybenzoic acid, para-hydroxybenzoic acid and hydroxypropionic acid.

The additional diol may be chosen in particular from the aliphatic diols such as propylene glycol, butylene glycol, hexylene glycol, diethylene glycol, polyethylene glycol; the aromatic diols such as hydroquinone, catechol, naphthalenediol, resorcinol, bisphenol A; alicyclic diols such as cyclohexanedimethanol.

Other comonomers may also be chosen from polyvalent carboxylic acids such as trimellitic acid, pyromellitic acid, tricarballylic acid; polyhydric alcohols such as glycerin, trimethylolethane, trimethylolpropane and pentaerythritol.

The polymethyl methacrylate may comprise acid monomers such that the acid value of the polymer is preferably greater than 3, in particular ranging from 3 to 20, and better still from 4 to 15. Such acid monomers may be (meth)acrylic acid or maleic acid.

The polyamide may be chosen from nylon 6, nylon 6-6, nylon 6-12, nylon 11, nylon 12, whose chemical composition is well known to persons skilled in the art.

Advantageously, in the multilayer structure of the flat fibres, the first polymer may be chosen from polyesters such as polyethylene terephthalate, polyethylene naphthalate, polycarbonate, in particular those defined above; the second polymer may be chosen from acrylic polymers such as polymethyl methacrylate, and the polyamides, in particular those described above.

The flat fibres with multilayer structure may comprise a protective layer which may comprise a polymer chosen from the layer polymers. Preferably, the polymer of the protective layer may have a refractive index ranging from 1.35 to 1.55.

The thickness of the protective layer may be greater than the thickness of the layers of polymers of the multilayer part.

The thickness of the protective layer may range from 2 μm to 10 μm, preferably from 2 μm to 7 μm.

When the fibre comprises, at the surface, a protective layer, this protective layer is taken into account for calculating the flattening factor.

As polymer of the protective layer, there may be used in particular polytetrafluoroethylene, tetrafluoroethylene/propylene copolymers, tetrafluoroethylene/hexafluoropropylene copolymers, tetrafluoroethylene/ethylene copolymers, tetrafluoroethylene/tetrafluoropropylene copolymers, polyvinylidene fluoride, polypentadecafluorooctyl acrylates, polyfluoroethyl acrylates, polytrifluoroisopropyl methacrylates, polytrifluoroethyl methacrylates, polyethyl acrylates, polyethyl methacrylates. It is also possible to use silicone polymers such as polydimethylsilanes, polydimethylsiloxanes; polyurethanes.

The flat fibres may be obtained in a known manner by extrusion of the polymer(s) through a die of rectangular shape and then cutting the thread obtained to the desired length.

As flat fibres, there may be used the interferential fibres sold under the names "Morphotex"<<Teijin Tetron Morphotex>> by the company TEIJIN. Such flat fibres are described in application EP-A-921217 whose content is integrated by way of reference into the present application.

The flat fibres may be present in the composition according to the invention, in particular in the top composition, in an amount ranging from 0.01% to 50% by weight, relative to the total weight of the composition, preferably from 0.1% to 30% by weight, and better still from 0.3% to 20% by weight.

The composition of the invention containing the flat fibres may be provided in the form of a product to be applied to the skin, the lips and/or the superficial body growths of human beings. It therefore contains a cosmetically acceptable medium, that is to say a medium compatible with all keratinous materials such as the skin both of the human body and of the face, the nails, the hair, the eyelashes and eyebrows.

According to the invention, this medium contains a lipophilic continuous phase, that is to say a mixture of one or more fatty substances or of organic solvents, immiscible with water or miscible at less than 50% by weight in water at room temperature (25° C.), which may be liquid, pasty or solid at room temperature (25° C. in general). In particular, this medium may comprise or may be provided in particular in the form of a suspension, dispersion or solution in an oily phase or of a lipophilic organic solvent, optionally thickened, or even gelled; suspension or dispersion in a waxy phase; water-in-oil (W/O) or multiple (O/W/O) emulsion in the form of a cream or a paste; anhydrous gel or oily foam; emulsified gel; two-phase or multiphase lotion; spray; powder; anhydrous paste. Persons skilled in the art will be able to choose the appropriate galenic form, as well as its method of preparation, on the basis of their general knowledge, taking into account, on the one hand, the nature of the constituents used, in particular their solubility in the carrier, and, on the other hand, the application envisaged for the composition.

The composition therefore comprises a lipophilic continuous phase which may contain fatty substances which are liquid at room temperature and atmospheric pressure, often called oils, organic solvents which are immiscible with water, waxes, gums, pasty fatty substances or a mixture of these constituents. This continuous phase may represent from 0.5 to 99.99% of the total weight of the composition.

In the kit according to the invention, the first composition, termed base composition, may comprise, as cosmetically acceptable medium, an aqueous medium or an organic solvent medium.

As fatty substances which are liquid at room temperature, often called oils, which can be used in the invention, there may be mentioned: hydrocarbon oils of animal origin such as perhydrosqualene; vegetable hydrocarbon oils such as liquid triglycerides of fatty acids with 4 to 10 carbon atoms such as the triglycerides of heptanoic or octanoic acids, or sunflower, maize, soyabean, grapeseed, sesame, apricot, macadamia, castor and avocado oils, the triglycerides of caprylic/capric acids, jojoba oil, shea butter; linear or branched hydrocarbons, of mineral or synthetic origin, such as paraffin oils and derivatives thereof, petroleum jelly, polydecenes, hydrogenated polyisobutene such as parleam; synthetic esters and ethers in particular of fatty acids or of fatty alchols having from 8 to 26 carbon atoms, such as for example Purcellin oil, isopropyl myristate, 2-ethylhexyl palmitate, 2-octyldodecyl stearate, 2-octyldodecyl erucate, isostearyl isostearate; esters of hydroxylated fatty acids or fatty alcohols such as isostearyl lactate, octyl hydroxystearate, octyldodecyl hydroxystearate, diisostearyl malate, triisocetyl citrate, heptanoates, octanoates, decanoates of fatty alcohols; polyol esters such as propylene glycol dioctanoate, neopentyl glycol diheptanoate, diethylene glycol diisononanoate; and pentaerythritol esters; fatty alcohols having from 12 to 26 carbon atoms such as octyl dodecanol, 2-butyloctanol, 2-hexyldecanol, 2-undecylpentadecanol, oleyl alcohol; partially hydrocarbon- and/or silicone-based fluorinated oils; silicone oils such as polymethylsiloxanes (PDMS) which are volatile or otherwise, linear or cyclic, liquid or pasty at room temperature such as cyclomethicones, dimethicones, optionally comprising a phenyl group, such as phenyl trimethicones, phenyltrimethylsiloxydiphenyl siloxanes, diphenylmethyldimethyl trisiloxanes, diphenyl dimethicones, phenyl dimethicones, polymethylphenyl siloxanes; mixtures thereof.

These oils may represent from 0 to 99.99% by weight relative to the total weight of the fatty phase.

The lipophilic continuous phase of the composition according to the invention may also comprise one or more cosmetically acceptable organic solvents (acceptable tolerance, toxicology and feel). These organic solvents may represent from 0 to 90% of the total weight of the composition and may be chosen from the group consisting of lipophilic organic solvents, amphiphilic solvents or mixtures thereof. As organic solvents which can be used in the composition of the invention, there may be mentioned acetic acid esters such as methyl, ethyl, butyl, amyl, 2-methoxyethyl or isopropyl acetate; ketones such as methyl ethyl ketone, methyl isobutyl ketone; hydrocarbons such as toluene, xylene, hexane, heptane; aldehydes having from 5 to 10 carbon atoms; ethers having at least 3 carbon atoms, and mixtures thereof.

When the composition according to the invention, or one of the base and/or top compositions, is provided in the form of an emulsion, it may optionally comprise, in addition, a surfactant, preferably in a quantity of 0 to 30% and in particular from 0.01 to 30% by weight relative to the total weight of the composition.

According to the application envisaged, the composition according to the invention, and in particular the first and/or second composition, may comprise, in addition, a film-forming polymer. The film-forming polymer may be a polymer solubilized or dispersed in the form of particles in the lipophilic continuous phase of the composition; it may also be solubilized or dispersed in an aqueous phase. The composition may comprise a mixture of these polymers.

The film-forming polymer may be present in the composition according to the invention, or one of the base and/or top compositions, in a polymer dry matter content ranging from 0.1% to 60% by weight relative to the total weight of the composition, preferably from 0.5% to 40% by weight, and better still from 1% to 30% by weight.

In the present application, the expression "film-forming polymer" is understood to mean a polymer capable of forming, on its own or in the presence of a film-forming aid, a continuous and adherent film on a support, in particular on keratinous materials.

Among the film-forming polymers which can be used in the composition of the present invention, there may be mentioned synthetic polymers of the free-radical type or of the polycondensate type, polymers of natural origin and mixtures thereof.

The expression free-radical film-forming polymer is understood to mean a polymer obtained by polymerization of monomers with in particular ethylenic unsaturation, each monomer being capable of homopolymerizing (in contrast to polycondensates). The film-forming polymers of the free-radical type may be in particular vinyl polymers or copolymers, in particular acrylic polymers.

The vinyl film-forming polymers may result from the polymerization of ethylenically unsaturated monomers having at least one acid group and/or esters of these acid monomers and/or amides of these acid monomers.

As a monomer carrying an acid group, there may be used α,β-ethylenic unsaturated carboxylic acids such as acrylic acid, methacrylic acid, crotonic acid, maleic acid or itaconic acid. (Meth)acrylic acid and crotonic acid are preferably used, and more preferably (meth)acrylic acid.

The esters of acid monomers are advantageously chosen from the esters of (meth)acrylic acid (also called (meth)acrylates), especially alkyl, in particular $C_1$-$C_{30}$, preferably $C_1$-$C_{20}$, alkyl, (meth)acrylates, aryl, in particular $C_6$-$C_{10}$ aryl, (meth)acrylates, hydroxyalkyl, in particular $C_2$-$C_6$ hydroxyalkyl, (meth)acrylates.

Among the alkyl (meth)acrylates, there may be mentioned methyl methacrylate, ethyl methacrylate, butyl methacrylate, isobutyl methacrylate, 2-ethylhexyl methacrylate, lauryl methacrylate and cyclohexyl methacrylate.

Among the hydroxyalkyl (meth)acrylates, there may be mentioned hydroxyethyl acrylate, 2-hydroxypropyl acrylate, hydroxyethyl methacrylate and 2-hydroxypropyl methacrylate.

Among the aryl (meth)acrylates, there may be mentioned benzyl acrylate and phenyl acrylate.

The esters of (meth)acrylic acid which are particularly preferred are the alkyl (meth)acrylates.

According to the present invention, the alkyl group of the esters may be either fluorinated or perfluorinated, that is to say that some or all of the hydrogen atoms of the alkyl group are substituted with fluorine atoms.

As amides of the acid monomers, there may be mentioned for example (meth)acrylamides, and especially N-alkyl (meth)acrylamides, in particular of $C_2$-$C_{12}$ alkyl. Among the N-alkyl(meth)acrylamides, there may be mentioned N-ethylacrylamide, N-t-butylacrylamide, N-t-octylacrylamide and N-undecylacrylamide.

The vinyl film-forming polymers may also result from the homopolymerization or copolymerization of monomers chosen from vinyl esters and styrene monomers. In particular, these monomers may be polymerized with acid monomers and/or their esters and/or their amides, such as those mentioned above.

As examples of vinyl esters, there may be mentioned vinyl acetate, vinyl neodecanoate, vinyl pivalate, vinyl benzoate and vinyl t-butyl benzoate.

As styrene monomers, there may be mentioned styrene and alpha-methylstyrene.

The list of monomers given is not limiting and it is possible to use any monomer known to a person skilled in the art entering into the categories of acrylic and vinyl monomers (including the monomers modified by a silicone chain).

Among the film-forming polycondensates, there may be mentioned polyurethanes, polyesters, polyester amides, polyamides, and epoxy ester resins and polyureas.

The polyurethanes may be chosen from anionic, cationic, nonionic or amphoteric polyurethanes, polyurethane-acrylics, polyurethane-polyvinylpyrrolidones, polyester-polyurethanes, polyetherpolyurethanes, polyureas, polyurea-polyurethanes and mixtures thereof.

The polyesters may be obtained, in a known manner, by polycondensation of dicarboxylic acids with polyols, in particular diols.

The dicarboxylic acid may be aliphatic, alicyclic or aromatic. There may be mentioned as examples of such acids: oxalic acid, malonic acid, dimethylmalonic acid, succinic acid, glutaric acid, adipic acid, pimelic acid, 2,2-dimethylglutaric acid, azelaic acid, suberic acid, sebacic acid, fumaric acid, maleic acid, itaconic acid, phthalic acid, dodecanedioic acid, 1,3-cyclohexanedicarboxylic acid, 1,4-cyclohexanedicarboxylic acid, isophthalic acid, terephthalic acid, 2,5-norbornanedicarboxylic acid, diglycolic acid, thiodipropionic acid, 2,5-naphthalenedicarboxylic acid and 2,6-naphthalenedicarboxylic acid. These dicarboxylic acid monomers may be used alone or in combination with at least two dicarboxylic acid monomers. Among these monomers, phthalic acid, isophthalic acid and terephthalic acid are preferably chosen.

The diol may be chosen from aliphatic, alicyclic or aromatic diols. A diol is preferably used which is chosen from: ethylene glycol, diethylene glycol, triethylene glycol, 1,3-propanediol, cyclohexanedimethanol and 4-butanediol. As other polyols, there may be used glycerol, pentaerythritol, sorbitol, trimethylolpropane.

The polyester amides may be obtained in a manner similar to the polyesters, by polycondensation of diacids with diamines or amino alcohols. As diamine, there may be used ethylenediamine, hexamethylenediamine, meta- or para-phenylenediamine. As amino alcohol, monoethanolamine may be used.

The polyester may, in addition, comprise at least one monomer carrying at least one —SO$_3$M group, with M representing a hydrogen atom, an ammonium ion NH$_4^+$ or a metal ion, such as for example an Na$^+$, Li$^+$, K$^+$, Mg$^{2+}$, Ca$^{2+}$, Cu$^{2+}$, Fe$^+$ or Fe$^{3+}$ ion. There may also be used in particular a bifunctional aromatic monomer comprising such an —SO$_3$M group.

The aromatic ring of the bifunctional aromatic monomer carrying, in addition, an —SO$_3$M group as described above may be chosen for example from benzene, naphthalene, anthracene, diphenyl, oxydiphenyl, sulphonyldiphenyl and methylenediphenyl rings. There may also be mentioned as examples of a bifunctional aromatic monomer carrying, in addition, an —SO$_3$M group: sulphoisophthalic acid, sulphoterephthalic acid, sulphophthalic acid, 4-sulphonaphthalene-2,7-dicarboxylic acid.

The use of copolymers based on isophthalate/sulphoisophthalate, and more particularly of copolymers obtained by condensation of diethylene glycol, cyclohexanedimethanol, isophthalic acid and sulphoisophthalic acid is preferred. Such polymers are sold, for example, under the trade name Eastman AQ® by the company Eastman Chemical Products.

The optionally modified polymers of natural origin may be chosen from shellac resin, sandarac gum, dammars, elemis, copals, water-insoluble cellulosic polymers such as nitrocellulose, cellulose acetate, cellulose acetobutyrate, cellulose acetopropionate, ethyl cellulose, and mixtures thereof.

According to a first embodiment of the composition according to the invention, the film-forming polymer may be present in the form of surface-stabilized particles dispersed in the liquid fatty phase. The film-forming polymer particles may have a size ranging from 5 nm to 600 nm, and in particular ranging from 20 nm to 300 nm. The techniques for preparing these dispersions are well known to persons skilled in the art. Dispersions of film-forming polymer in the liquid fatty phase, in the presence of stabilizing agents, are in particular described in the documents EP-A-749746, EP-A-923928, EP-A-930060 whose content is incorporated by way of reference into the present application.

According to a second embodiment of the composition according to the invention, the film-forming polymer may be solubilized in the liquid fatty phase; the film-forming polymer is then said to be a fat-soluble polymer.

By way of example of fat-soluble polymer, there may be mentioned the polymers corresponding to the following formula (I):

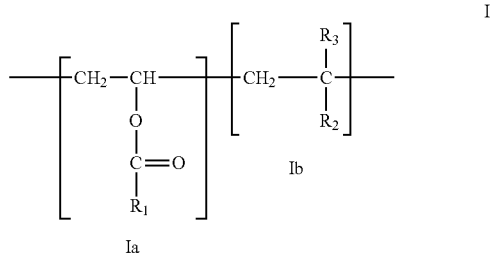

in which:
R$_1$ represents a saturated, linear or branched, hydrocarbon chain having from 1 to 19 carbon atoms;
R$_2$ represents a radical taken from the group consisting of:
a) —O—CO—R$_4$, R$_4$ having the same meaning as R$_1$ but is different from R$_1$ in the same copolymer,
b) —CH$_2$—R$_5$, R$_5$ representing a saturated, linear or branched, hydrocarbon chain having from 5 to 25 carbon atoms,
c) —O—R$_6$, R$_6$ representing a saturated hydrocarbon chain having from 2 to 18 carbon atoms, and
d) —CH$_2$—O—CO—R$_7$, R$_7$ representing a saturated, linear or branched, hydrocarbon chain having from 1 to 19 carbon atoms,
R$_3$ represents a hydrogen atom when R$_2$ represents the radicals a), b) or c) or R$_3$ represents a methyl radical when R$_2$ represents the radical d), it being necessary for the said copolymer to consist of at least 15% by weight of at least one monomer derived from a unit (Ia) or from a unit (Ib) in which the saturated, linear or branched, hydrocarbon chains have at least 7 carbon atoms.

The copolymers of formula (I) result from the copolymerization of at least one vinyl ester (corresponding to the unit Ia)

and of at least one other monomer (corresponding to the unit Ib) which may be an α-olefin, an alkyl vinyl ether or an allyl or methallyl ester.

When, in the unit (Ib), $R_2$ is chosen from the radicals —$CH_2$—$R_5$, —O—$R_6$ or —$CH_2$—O—CO—$R_7$ as defined above, the copolymer of formula (I) may consist of 50 to 95 mol % of at least one unit (Ia) and of 5 to 50 mol % of at least one unit (Ib).

The copolymers of formula (I) may also result from the copolymerization of at least one vinyl ester and at least one other vinyl ester different from the first. In this case, these copolymers may consist of 10 to 90 mol % of at least one unit (Ia) and of 10 to 90 mol % of at least one unit (Ib) in which $R_2$ represents the radical —O—CO—$R_4$.

Among the vinyl esters leading to the unit of formula (Ia), or to the unit of formula (Ib) in which $R_2$=—O—CO—$R_4$, there may be mentioned vinyl acetate, vinyl propionate, vinyl butanoate, vinyl octanoate, vinyl decanoate, vinyl laurate, vinyl stearate, vinyl isostearate, vinyl 2,2-dimethyloctanoate and vinyl dimethylpropionate.

Among the α-olefins leading to the unit of formula (Ib) in which $R_2$=—$CH_2$—$R_5$, there may be mentioned 1-octene, 1-dodecene, 1-octadecene, 1-eicosene and mixtures of α-olefins having from 22 to 28 carbon atoms.

Among the alkyl vinyl ethers leading to the unit of formula (Ib) in which $R_2$=—O—$R_6$, there may be mentioned ethyl vinyl ether, n-butyl vinyl ether, isobutyl vinyl ether, decyl vinyl ether, dodecyl vinyl ether, cetyl vinyl ether and octadecyl vinyl ether.

Among the allyl or methallyl esters leading to the unit of formula (Ib) in which $R_2$=—$CH_2$—O—CO—$R_7$, there may be mentioned allyl and methallyl acetates, propionates, dimethylpropionates, butyrates, hexanoates, octanoates, decanoates, laurates, 2,2-dimethylpentanoates, stearates and eicosanoates.

The copolymers of formula (I) may also be crosslinked using certain types of crosslinking agents which are intended to substantially increase their molecular weight.

This crosslinking is carried out during the copolymerization and the crosslinking agents may be either of the vinyl type or of the allyl or methallyl type. Among these, there may be mentioned in particular tetraallyloxyethane, divinylbenzene, divinyl octanedioate, divinyl dodecanedioate and divinyl octadecanedioate.

Among the various copolymers of formula (I) which can be used in the composition according to the invention, there may be mentioned the copolymers: vinyl acetate/allyl stearate, vinyl acetate/vinyl laurate, vinyl acetate/vinyl stearate, vinyl acetate/octadecene, vinyl acetate/octadecyl vinyl ether, vinyl propionate/allyl laurate, vinyl propionate/vinyl laurate, vinyl stearate/1-octadecene, vinyl acetate/1-dodecene, vinyl stearate/ethyl vinyl ether, vinyl propionate/cetyl vinyl ether, vinyl stearate/allyl acetate, vinyl 2,2-dimethyloctanoate/vinyl laurate, allyl 2,2-dimethylpentanoate/vinyl laurate, vinyl dimethyl propionate/vinyl stearate, allyl dimethyl propionate/vinyl stearate, vinyl propionate/vinyl stearate, crosslinked with 0.2% of divinylbenzene, vinyl dimethyl propionate/vinyl laurate, crosslinked with 0.2% of divinylbenzene, vinyl acetate/octadecyl vinyl ether, crosslinked with 0.2% of tetraallyloxyethane, vinyl acetate/allyl stearate, crosslinked with 0.2% of divinylbenzene, vinyl acetate/1-octadecene crosslinked with 0.2% of divinylbenzene and allyl propionate/allyl stearate crosslinked with 0.2% of divinylbenzene.

As fat-soluble film-forming polymers, there may also be mentioned fat-soluble homopolymers, and in particular those resulting from the homopolymerization of vinyl esters having from 9 to 22 carbon atoms or of alkyl acrylates or methacrylates, the alkyl radicals having from 10 to 20 carbon atoms.

Such fat-soluble homopolymers may be chosen from polyvinyl stearate, polyvinyl stearate crosslinked using divinylbenzene, diallyl ether or diallyl phthalate, polystearyl (meth) acrylate, polyvinyl laurate, polylauryl (meth)acrylate, it being possible for these poly(meth)acrylates to be crosslinked using ethylene glycol or tetraethylene glycol dimethacrylate.

The fat-soluble copolymers and homopolymers defined above are known and in particular described in application FR-A-2262303; they may have a weight-average molecular weight ranging from 2 000 to 500 000, and preferably from 4 000 to 200 000.

As fat-soluble film-forming polymers which can be used in the invention, there may also be mentioned polyalkylenes and in particular copolymers of $C_2$-$C_{20}$ alkenes, different from the polyolefin wax defined in a), such as polybutene, alkyl celluloses with a saturated or unsaturated, linear or branched, $C_1$ to $C_8$ alkyl radical such as ethyl cellulose or propyl cellulose, copolymers of vinylpyrrolidone (VP) and in particular copolymers of vinylpyrrolidone and of a $C_2$ to $C_{40}$, and better still $C_3$ to $C_{20}$, alkene. By way of example of VP copolymers which can be used in the invention, there may be mentioned the VP/vinyl acetate, VP/ethyl methacrylate, butylated polyvinylpyrrolidone (PVP), VP/ethyl methacrylate/methacrylic acid, VP/eicosene, VP/hexadecene, VP/triacontene, VP/styrene and VP/acrylic acid/lauryl methacrylate copolymers.

The film-forming polymer is used in particular when it is desired to prepare a composition of the type including nail varnish, mascara, eyeliner, lacquer for the eyebrows, or hair, in particular hairstyling, compositions.

The film-forming polymer may be combined with film-forming aids. Such an aid may be chosen from any of the compounds known to persons skilled in the art as being capable of fulfilling the desired function, and may be chosen in particular from plasticizers and coalescents.

The composition according to the invention, or one of the base and/or top compositions, may also comprise an aqueous, alcoholic or aqueous-alcoholic phase, in a form dispersed or emulsified in the continuous phase. This phase may contain water, alcohols, a mixture of water and of alcohol or of acetone. The alcohols are in particular linear or branched lower monoalcohols having from 2 to 5 carbon atoms such as ethanol or propanol, polyols such as glycerin, diglycerin, propylene glycol, sorbitol, penthenol, penthylene glycol, polyethylene glycols. This aqueous phase may represent from 0 to 90% of the weight of the composition. It may, in addition, contain $C_2$ ethers and $C_2$-$C_4$ aldehydes.

The composition according to the invention, or one of the base and/or top compositions, may furthermore comprise all the ingredients conventionally used in the fields considered and more especially in the cosmetic and dermatological fields. These ingredients are in particular chosen from preservatives, thickeners, perfumes, hydrophilic or lipophilic active agents and mixtures thereof. The quantities of these different ingredients are those conventionally used in the fields considered and for example from 0.01% to 20% of the total weight of the composition.

The composition of the invention, or the top composition, may in addition comprise an additional particulate phase which may be present in an amount of 0 to 48% (in particular 0.01% to 48%) of the total weight of the composition, preferably from 0.01% to 30% and better still from 0.02% to 20%, and which may comprise pigments and/or pearlescent agents and/or fillers used in the cosmetic compositions.

The expression pigments should be understood to mean white or coloured, mineral or organic particles which are insoluble in the liquid fatty phase, intended to colour and/or opacify the composition. The expression fillers should be understood to mean colourless or white, mineral or synthetic, lamellar or nonlamellar particles. The expression pearlescent agents should be understood to mean irridescent particles, in particular produced by certain molluscs in their shell, or synthesized. These fillers and pearlescent agents serve in particular to modify the texture of the composition.

The pigments may be present in the composition in an amount of 0 to 25% (in particular 0.01% to 25%) relative to the weight of the composition, preferably from 0.01% to 15% by weight, and better still from 0.02% to 5% by weight. As mineral pigments which can be used in the invention, there may be mentioned titanium, zirconium or cerium oxides and zinc, iron or chromium oxides and ferric blue. Among the organic pigments which can be used in the invention, there may be mentioned carbon black, and barium, strontium, calcium and aluminium lacquers or diketopyrrolopyrrole (DPP) described in the documents EP-A-542669, EP-A-787730, EP-A-787731 and WO-A-96/08537.

The pearlescent agents may be present in the composition in an amount of 0 to 25% (in particular 0.01% to 25%) by weight, relative to the total weight of the composition, preferably from 0.01% to 15% by weight, and better still from 0.02% to 5% by weight. Among the pearlescent agents which can be used in the invention, there may be mentioned mica coated with titanium oxide, iron oxide, natural pigment or bismuth oxychloride such as coloured mica-titanium.

The fillers may be present in an amount of 0 to 48% by weight, relative to the total weight of the composition, preferably 0.01 to 30% by weight, and better still from 0.02% to 20% by weight. There may be mentioned in particular talc, zinc stearate, mica, kaolin, polyamide powders (Nylon®) (Orgasol® from Atochem), polyethylene powders, powders of tetrafluoroethylene polymers (Teflon®), starch, boron nitride, polymeric microspheres such as those of polyvinylidene chloride/acrylonitrile such as Expancel® (Nobel Industrie), acrylic acid copolymers (Polytrap® from the company Dow Corning) and microbeads of silicone resin (Tospearls® from Toshiba, for example), elastomeric organopolysiloxanes.

The composition may also comprise water-soluble or fat-soluble colorants in an amount ranging from 0 to 6% (in particular 0.01% to 6%) by weight, relative to the total weight of the composition, preferably ranging from 0.01% to 3% by weight. The fat-soluble colorants are for example Sudan red, DC Red 17, DC Green 6, β-carotene, soyabean oil, Sudan brown, DC Yellow 11, DC Violet 2, DC orange 5, quinoline yellow. The water-soluble colorants are for example beet juice or methylene blue.

According to a preferred mode of the make-up kit and method according to the invention, the base composition is coloured with the colouring matter and the top composition may comprise a substantially transluscent medium such that the said medium does not mask the colour of the flat fibres. The application of the base composition to the keratinous materials and then of the top composition then leads to a make-up which distinctly reveals the flat fibres distributed over the coloured layer obtained with the base composition. A contrast is thereby observed between the colours of the flat fibres and the colour of the base layer.

The colouring matter present in the first base composition of the make-up kit and method may be chosen from water-soluble or fat-soluble pigments, pearlescent agents and colorants as defined above, in the amounts indicated.

The composition of the invention, or one of the base and/or top compositions, may comprise one or more gums and/or one or more waxes. The waxes may be hydrocarbon-based, fluorinated and/or silicone-based and may be of plant, mineral, animal and/or synthetic origin. In particular the waxes have a melting point greater than 25° C. and better still greater than 45° C.

As wax which can be used in the composition of the invention, there may be mentioned beeswax, Carnauba or Candelilla wax, paraffin, microcrystalline waxes, ceresin or ozokerite; synthetic waxes such as polyethylene or Fischer Tropsch waxes, silicone waxes such as alkyl or alkoxy dimethicone having from 16 to 45 carbon atoms.

The gums are generally PDMSs of high molecular weight or cellulose gums or polysaccharides and the pasty substances are generally hydrocarbon compounds such as lanolins and derivatives thereof or PDMSs.

The nature and the quantity of the solid substances depend on the desired mechanical properties and textures. As a guide, the composition, or one of the base and/or top compositions, may contain from 0 to 50% by weight of waxes, relative to the total weight of the composition, and better still from 1 to 30%.

This composition may have the appearance of a cream, ointment, fluid lotion, soft paste (in particular paste having a dynamic viscosity at 25° C. of the order of 0.1 to 40 Pa.s at a shear rate of 200 s$^{-1}$, after 10 minutes of measurement in a cone/planar geometry), or unguent.

The composition according to the invention, or one of the base and/or top compositions, may also contain ingredients commonly used in cosmetics, such as vitamins, thickeners, trace elements, emollients, sequestrants, perfumes, alkalinizing or acidifying agents, preservatives, UV-screening agents, or mixtures thereof.

Of course, persons skilled in the art will be careful to choose this or these optional additional compounds, and/or their quantity, so that the advantageous properties of the composition according to the invention are not, or not substantially, impaired by the addition envisaged.

The composition of the invention, in particular the base and top compositions, may be obtained according to the methods of preparation conventionally used in the cosmetics or dermatological field.

Advantageously, the base and top compositions are packaged in separate compartments or containers which may be accompanied by identical or different appropriate application means such as fine brushes, coarse brushes, feathers, sponges or nonwoven materials (paper, patch).

The top composition comprising the flat fibres may be applied either at one of the ends of the base layer, or in the middle, or discontinuously, in particular in the form of geometrical, symmetrical or asymmetrical motifs (for example in the form of dots, squares, circles, stars), distributed in a random or orderly manner, with distinct or indistinct contours.

The examples of compositions below are given by way of illustration and without limitation.

EXAMPLE 1

A nail varnish base composition was prepared comprising:

| | |
|---|---|
| nitrocellulose | 19 g |
| N-ethyl o,p-toluenesulphonamide | 6 g |
| tributyl acetyl citrate | 6 g |
| midnight blue pigments | 1 g |
| hectorite | 1.2 g |

-continued

| | |
|---|---|
| isopropyl alcohol | 8 g |
| ethyl acetate, butyl acetate | qs 100 g |

A top composition (nail varnish) with a transluscent medium was also prepared comprising:

| | |
|---|---|
| nitrocellulose | 17.1 g |
| N-ethyl o,p-toluenesulphonamide | 5.4 g |
| tributyl acetyl citrate | 5.4 g |
| interferential fibres of polyethylene terephthalate and of nylon having a length of 0.3 mm sold under the name "Morphotex" by the company TEIJIN | 10 g |
| hectorite | 1.0 g |
| isopropyl alcohol | 7.2 g |
| ethyl acetate, butyl acetate | qs 100 g |

The interferential fibres are well dispersed homogeneously in the nail varnish solvent medium.

The midnight blue-coloured base composition was applied to the nails and then, after drying of the deposited layer, the top composition was applied thereto. After drying, a make-up is obtained exhibiting a homogeneous deposit of flat fibres with a colour effect on a midnight blue base.

EXAMPLE 2

A composition A was prepared comprising:

| | |
|---|---|
| nitrocellulose | 11.2 g |
| tosylamide/sulphonamide resin | 11.1 g |
| plasticizers | 6.8 g |
| hectorite | 1.1 g |
| ethyl acetate, butyl acetate, isopropyl alcohol | qs 100 g |

A composition B was prepared comprising:

| | |
|---|---|
| interferential fibres of polyethylene terephthalate and of nylon having a length of 0.3 mm sold under the name "Morphotex" by the company TEIJIN | 10 g |
| Composition A | 90 g |

The viscoelastic properties of the film obtained with compositions A and B was evaluated.

The viscoelastic properties of the film are measured during dynamic trials under sinusoidal actions of low amplitude (small deformations) performed at 30° C. over a frequency range of 0.1 to 20 Hz on a viscoelasticimeter, for example of the DMA 2980 type from T.A. Instruments in traction on film. For this, each mixture is applied to a teflon-based matrix and then, after drying at 30° C. for 24 hours, the film formed is recovered. The modulus of elasticity in traction E' of the film, expressed in MPa, is then measured.

The following results were obtained:

| Composition | Thickness of the film (μm) | E' at 0.1 Hz (in MPa) | E' at 0.1 Hz (in MPa) | E' at 5 Hz (in MPa) | E' at 20 Hz (in MPa) |
|---|---|---|---|---|---|
| Composition A | 170 | 6 | 29 | 89 | 203 |
| Composition B | 310 | 25 | 76 | 167 | 296 |

It is observed that the modulus of elasticity measured at each frequency of the film obtained with composition B comprising the flat fibres is higher than that of the film obtained with composition A. Thus, the presence of flat fibres in composition B makes it possible to obtain a film exhibiting reinforced mechanical, in particular elastic, properties.

The invention claimed is:

1. A nail varnish comprising, in a cosmetically acceptable medium, at least one lipophilic continuous phase, said phase containing flat fibers,
   wherein said flat fibers have a cross section having a longer length L1, and a shorter length L2, such that the ratio L1/L2 is greater than 4,
   wherein said flat fibers are of synthetic origin,
   wherein said flat fibers have a cross-section shape chosen from ovoid and/or ellipsoid; and
   wherein said flat fibers are in the form of unitary fibers.

2. The nail varnish according to claim 1, wherein the flat fibers have a length L and a diameter D such that the ratio L/D ranges from 1.2 to 2,500.

3. The nail varnish according to claim 2, wherein the ratio L/D ranges from 1.5 to 500.

4. The nail varnish according to claim 3, wherein the ratio L/D ranges from 1.6 to 150.

5. The nail varnish according to claim 1, wherein the flat fibers have a diameter D ranging from 2 nm to 500 μm.

6. The nail varnish according to claim 5, wherein the flat fibers have a diameter D ranging from 2 nm to 500 μm, wherein D is the diameter of the circle in which the section of the fiber is inscribed.

7. The nail varnish according to claim 6, wherein the flat fibers have a diameter D ranging from 100 nm to 100 μm.

8. The nail varnish according to claim 7, wherein the flat fibers have a diameter D ranging from 1 μm to 70 μm.

9. The nail varnish according to claim 1, wherein the flat fibers have a length L ranging from 1 μm to 10 mm.

10. The nail varnish according to claim 9, wherein the flat fibers have a length L ranging from 0.1 mm to 5 mm.

11. The nail varnish according to claim 10, wherein the flat fibers have a length L ranging from 0.3 mm to 3.5 mm.

12. The nail varnish according to claim 1, wherein the ratio L1/L2 is greater than 7.

13. The nail varnish according to claim 1, wherein the ratio L1/L2 ranges from 4 to 15.

14. The nail varnish according to claim 13, wherein the ratio L1/L2 ranges from 6 to 12.

15. The nail varnish according to claim 14, wherein the ratio L1/L2 ranges from 7 to 10.

16. The nail varnish according to claim 1, wherein the flat fibers are in a form chosen from ribbons and tagliatelle.

17. The nail varnish according to claim 1, wherein the flat fibers are twisted along the axis of the length L of the fibers.

18. The nail varnish according to claim 1, wherein the flat fibers have a titre ranging from 0.15 to 30 denier.

19. The nail varnish according to claim 18, wherein the flat fibers have a titre ranging from 0.18 to 18 denier.

20. The nail varnish according to claim 1, wherein the flat fibers are polymer fibers.

21. The nail varnish according to claim 20, wherein the polymer fibers are chosen from rayon fibers, polyamide fibers, viscose fibers, acetate fibers, poly(p-phenyleneterephthalamide) fibers, acrylic fibers, polyolefin fibers, polytetrafluoroethylene fibers, polyvinyl chloride fibers, polyvinylidene chloride fibers, polyvinylidene fluoride fibers, polyvinyl alcohol fibers, polyacrylonitrile fibers, polyurethane fibers, polyester fibers, and polycarbonate fibers.

22. The nail varnish according claim 21, wherein the acetate fibers comprise rayon acetate fibers.

23. The nail varnish according to claim 21, wherein the acrylic fibers are chosen from polymethyl methacrylate fibers and poly-2-hydroxyethyl methacrylate fibers.

24. The nail varnish according to claim 21, wherein the polyolefin fibers are chosen from polyethylene fibers and polypropylene fibers.

25. The nail varnish according to claim 21, wherein the polyester fibers are chosen from polyethylene terephthalates and polyethylene naphthalates.

26. The nail varnish according to claim 21, wherein the flat fibers are chosen from polyester, acrylic polymer and polyamide fibers.

27. The nail varnish according to claim 20, wherein the flat fibers comprise a polymer chosen from polyethylene terephthalate, polyethylene naphthalate, polycarbonate, polymethyl methacrylate, nylon 6, nylon 6-6, nylon 6-12, nylon 11, and nylon 12.

28. The nail varnish according to claim 1, wherein the flat fibers comprise a multilayer structure of polymers having alternate layers of at least one first polymer and at least one second polymer.

29. The nail varnish according to claim 28, wherein the alternate layers of polymers of the flat fibers are such that they allow the creation of a color effect by interferences of light rays, which diffract and diffuse differently according to the layers.

30. The nail varnish according to claim 28, wherein each layer of polymer is in a plane (P) parallel to the direction of the principal axis of the fiber, in the direction of its length L.

31. The nail varnish according to claim 28, wherein the multilayer fiber comprises at least 5 individual layers of polymer.

32. The nail varnish according to claim 31, wherein the multilayer fiber comprises individual layers of polymer ranging from 5 to 120 layers.

33. The nail varnish according to claim 32, wherein the multilayer fiber comprises at least 10 individual layers of polymer.

34. The nail varnish according to claim 33, wherein the multilayer fiber comprises individual layers of polymer ranging from 10 to 70 layers.

35. The nail varnish according to claim 34, wherein the multilayer fiber comprises individual layers of polymer ranging from 10 to 50 layers.

36. The nail varnish according to claim 28, wherein each layer of the at least one first and at least one second polymer has a thickness $d_1$, and $d_2$, respectively, which may be identical or different, ranging from 0.02 μm to 0.3 μm.

37. The nail varnish according to claim 36, wherein the thicknesses, $d_1$, and $d_2$, which may be identical or different, range from 0.05 μm to 0.15 μm.

38. The nail varnish according to claim 28, wherein the polymers present in the fibers have a refractive index ranging from 1.30 to 1.82.

39. The nail varnish according to claim 38, wherein the polymers present in the fibers have a refractive index ranging from 1.35 to 1.75.

40. The nail varnish according to claim 28, wherein the at least one first and at least one second polymer have a refractive index $n_1$ and $n_2$, respectively, such that the ratio $n_1/n_2$ ranges from 1.1 to 1.4.

41. The nail varnish according to claim 28, wherein the flat fibers with multilayer structures have a reflection spectrum such that the width at half height of the spectrum $\lambda_{L=1/2}$ ranges from 0 to 200 nm.

42. The nail varnish according to claim 28, wherein the at least one first polymer is a polyester and the at least one second polymer is a polyamide.

43. The nail varnish according to claim 1, wherein the flat fibers are surface-treated or coated with a protective layer.

44. The nail varnish according to claim 43, wherein the protective layer comprises a polymer chosen from polyurethanes, polyethyl acrylates, and polyethyl methacrylates.

45. The nail varnish according to claim 44, wherein the polymer comprising the protective layer has a refractive index ranging from 1.35 to 1.55.

46. The nail varnish according to claim 1, wherein the flat fibers are present in the composition in an amount ranging from 0.01% to 50% by weight, relative to the total weight of the composition.

47. The nail varnish according to claim 46, wherein the flat fibers are present in the composition in an amount ranging from 0.1% to 30% by weight, relative to the total weight of the composition.

48. The nail varnish according to claim 47, wherein the flat fibers are present in the composition in an amount ranging from 0.3% to 20% by weight, relative to the total weight of the composition.

49. The nail varnish according to claim 1, wherein the at least one lipophilic continuous phase comprises at least one fatty substance chosen from waxes, gums, pasty fatty substances, and lipophilic organic solvents.

50. The nail varnish according to claim 1, further comprising at least one film-forming polymer.

51. The nail varnish according to claim 50, wherein the at least one film-forming polymer is chosen from vinyl polymers, polyurethanes, polyesters, polyamides, and polyureas.

52. The nail varnish according to claim 50, wherein the at least one film-forming polymer is dissolved or dispersed in the form of particles in the lipophilic continuous phase.

53. The nail varnish according to claim 50, wherein the at least one film-forming polymer is present in the composition in a polymer dry matter amount ranging from 0.1% to 60% by weight, relative to the total weight of the composition.

54. The nail varnish according to claim 50, wherein the at least one film-forming polymer is present in the composition in a polymer dry matter amount ranging from 0.5% to 40% by weight, relative to the total weight of the composition.

55. The nail varnish according to claim 50, wherein the at least one film-forming polymer is present in the composition in a polymer dry matter amount ranging from 1% to 30% by weight, relative to the total weight of the composition.

56. The nail varnish according to claim 1, further comprising at least one phase chosen from hydrophilic, aqueous, alcoholic and aqueous-alcoholic phases dispersed or emulsified in the at least one lipophilic continuous phase.

57. The nail varnish according to claim 1, further comprising an additional particulate phase, which is present in the composition an amount ranging from 0 to 48% by weight, relative to the total weight of the composition.

58. The nail varnish according to claim 57, further comprising an additional particulate phase, which is present in the composition an amount ranging from 0.01% to 30% by weight, relative to the total weight of the composition.

59. The nail varnish according to claim 58, further comprising an additional particulate phase, which is present in the composition an amount ranging from 0.02% to 20% by weight, relative to the total weight of the composition.

60. The nail varnish according to claim 57, wherein the at least one additional particulate phase is chosen from pigments, pearlescent agents and fillers.

61. The nail varnish according to claim 1, further comprising at least one cosmetic ingredient chosen from vitamins, thickeners, trace elements, emollients, sequestrants, perfumes, alkalinizing agents, acidifying agents, and preservatives.

62. A cosmetic method for making-up keratinous materials, comprising applying to the keratinous materials a nail varnish comprising, in a cosmetically acceptable medium, at least one lipophilic continuous phase, said phase containing flat fibers.

63. A cosmetic method for making-up keratinous materials, comprising applying to the keratinous materials a nail varnish comprising:
   a first layer of a first composition comprising, in a cosmetically acceptable medium, at least one coloring matter,
   applying, to at least a portion of the first layer, a second layer of a second composition comprising, in a cosmetically acceptable lipophilic continuous medium, flat fibers having a cross section having a longer length L1, and a shorter length L2, such that the ratio L1/L2 is greater than 4, wherein the flat fibers are of synthetic origin and have a cross-section shape chosen from ovoid and/or ellipsoid, and are in the form of unitary fibers, and wherein the first composition does not comprise the flat fibers present in the second composition.

64. The method according to claim 63, wherein the flat fibers have a length L and a diameter D such that the ratio L/D ranges from 1.2 to 2,500.

65. The method according to claim 64, wherein the ratio L/D ranges from 1.5 to 500.

66. The method according to claim 65, wherein the ratio L/D ranges from 1.6 to 150.

67. The method according to claim 63, wherein the flat fibers have a diameter D ranging from 2 nm to 500 µm, wherein D is the diameter of the circle in which the section of the fiber is inscribed.

68. The method according to claim 67, wherein the flat fibers have a diameter D ranging from 100 nm to 100 µm.

69. The method according to claim 68, wherein the flat fibers have a diameter D ranging from 1 µm to 70 µm.

70. The method according to claim 63, wherein the flat fibers have a length L ranging from 1 µm to 10 mm.

71. The method according to claim 70, wherein the flat fibers have a length L ranging from 0.1 mm to 5 mm.

72. The method according to claim 71, wherein the flat fibers have a length L ranging from 0.3 mm to 3.5 mm.

73. The method according to claim 63, wherein the ratio L1/L2 is greater than 7.

74. The method according to claim 63, wherein the ratio L1/L2 ranges from 4 to 15.

75. The method according to claim 74, wherein the ratio L1/L2 ranges from 6 to 12.

76. The method according to claim 75, wherein the ratio L1/L2 ranges from 7 to 10.

77. The method according to claim 63, wherein the flat fibers have a cross section shape chosen from rectangular, ovoid and ellipsoid.

78. The method according to claim 63, wherein the flat fibers are chosen from ribbons and tagliatelli.

79. The method according to claim 63, wherein the flat fibers are twisted along the axis of the length L of the fibers.

80. The method according to claim 63, wherein the flat fibers have a titre ranging from 0.15 to 30 denier.

81. The method according to claim 80, wherein the flat fibers have a titre ranging from 0.18 to 18 denier.

82. The method according to claim 63, wherein the flat fibers are polymer fibers.

83. The method according to claim 63, wherein the flat fibers are chosen from rayon fibers, polyamide fibers, viscose fibers, acetate fibers, poly(p-phenylene-terephthalamide) fibers, acrylic polymer fibers, polyolefin fibers, polytetrafluoroethylene fibers, polyvinyl chloride fibers, polyvinylidene chloride fibers, polyvinylidene fluoride fibers, polyvinyl alcohol fibers, polyacrylonitrile fibers, polyurethane fibers, polyester fibers, and polycarbonate fibers.

84. The method according to claim 83, wherein the acetate fibers comprise rayon acetate fibers.

85. The method according to claim 83, wherein the acrylic polymer fibers are chosen from polymethyl methacrylate fibers and poly-2-hydroxyethyl methacrylate fibers.

86. The method according to claim 83, wherein the polyolefin fibers are chosen from polyethylene and polypropylene fibers.

87. The method according to claim 83, wherein the polyester fibers are chosen from polyethylene terephthalates and polyethylene naphthalates.

88. The method according to claim 83, wherein the flat fibers are chosen from polyester, acrylic polymer and polyamide fibers.

89. The method according to claim 83, wherein the flat fibers comprise a polymer chosen from polyethylene terephthalate, polyethylene naphthalate, polycarbonate, polymethyl methacrylate, nylon 6, nylon 6-6, nylon 6-12, nylon 11, and nylon 12.

90. The method according to claim 63, wherein the flat fibers comprise a multilayer structure of polymers having alternate layers of at least one first polymer and at least one second polymer.

91. The method according to claim 90, wherein the alternate layers of polymers of the flat fibers are such that they allow the creation of a color effect by interferences of light rays, which diffract and diffuse differently according to the layers.

92. The method according to claim 90, wherein each layer of polymer is in a plane (P) parallel to the direction of the principal axis of the fiber, in the direction of its length L.

93. The method according to claim 90, wherein the multilayer fiber comprises at least 5 individual layers of polymer.

94. The method according to claim 90, wherein the multilayer fiber comprises at least 10 individual layers of polymer.

95. The method according to claim 93, wherein the multilayer fiber comprises individual layers of polymer ranging from 5 to 120 layers.

96. The method according to claim 94, wherein the multilayer fiber comprises individual layers of polymer ranging from 10 to 70 layers.

97. The method according to claim 96, wherein the multilayer fiber comprises individual layers of polymer ranging from 10 to 50 layers.

98. The method according to claim 90, wherein each layer of the at least one first and at least one second polymer has a thickness $d_1$, $d_2$, respectively, which may be identical or different, ranging from 0.02 μm to 0.3 μm.

99. The method according to claim 98, wherein the thicknesses $d_1$, and $d_2$, which may be identical or different, range from 0.05 μm to 0.15 μm.

100. The method according to claim 90, wherein the polymers present in the fibers have a refractive index ranging from 1.30 to 1.82.

101. The method according to claim 100, wherein the polymers present in the fibers have a refractive index ranging from 1.35 to 1.75.

102. The method according to claim 90, wherein the at least one first and at least one second polymers have a refractive index $n_1$ and $n_2$, respectively, such that the ratio $n_1/n_2$ ranges from 1.1 to 1.4.

103. The method according to claim 90, wherein the flat fibers with a multilayer structure have a reflection spectrum such that the width at half height of the spectrum, $\lambda_{L=1/2}$, ranges from 0 to 200 nm.

104. The method according to claim 90, wherein the at least one first polymer comprises a polyester and the at least one second polymer comprises a polyamide.

105. The method according claim 63, wherein the flat fibers are surface-treated or coated with a protective layer.

106. The method according to claim 105, wherein the protective layer comprises a polymer chosen from polyurethanes, polyethyl acrylates, and polyethyl methacrylates.

107. The method according to claim 63, wherein the flat fibers are present in the second composition in an amount ranging from 0.01% to 50% by weight, relative to the total weight of the second composition.

108. The method according to claim 107, wherein the flat fibers are present in the second composition in an amount ranging from 0.1% to 30% by weight, relative to the total weight of the second composition.

109. The method according to claim 108, wherein the flat fibers are present in the second composition in an amount ranging from 0.3% to 20% by weight, relative to the total weight of the second composition.

110. The method according to claim 63, wherein the at least one lipophilic continuous phase comprises at least one fatty substance chosen from oils, waxes, gums, pasty fatty substances, and lipophilic organic solvents.

111. The method according to claim 63, wherein at least one of the first and the second composition comprises a phase chosen from aqueous, alcoholic and aqueous-alcoholic phases, which is dispersed or emulsified in the lipophilic continuous phase.

112. The method according to claim 63, wherein at least one of the first and the second composition further comprises at least one film-forming polymer.

113. The method according to claim 112, wherein the at least one film-forming polymer is chosen from vinyl polymers, polyurethanes, polyesters, polyamides, and polyureas.

114. The method according to claim 112, wherein the at least one film-forming polymer is dissolved or dispersed in the form of particles in the lipophilic continuous phase.

115. The method according to claim 112, wherein the at least one film-forming polymer is present in a polymer dry matter amount ranging from 0.1% to 60% by weight, relative to the total weight of the composition.

116. The method according to claim 115, wherein the at least one film-forming polymer is present in a polymer dry matter amount ranging from 0.5% to 40% by weight, relative to the total weight of the composition.

117. The method according to claim 116, wherein the at least one film-forming polymer is present in a polymer dry matter amount ranging from 1% to 30% by weight, relative to the total weight of the composition.

118. The method according to claim 63, wherein the composition further comprises an additional particulate phase, which is present in an amount ranging from 0 to 48% by weight, relative to the total weight of the composition.

119. The method according to claim 118, wherein the additional particulate phase is present in an amount ranging from 0.01% to 30% by weight, relative to the total weight of the composition.

120. The method according to claim 119, wherein the additional particulate phase is present in an amount ranging from 0.02% to 20% by weight, relative to the total weight of the composition.

121. The method according to claim 118, wherein the additional particulate phase is chosen from pigments, pearlescent agents and fillers.

122. The method according to claim 63, wherein the second composition comprises a substantially translucent medium.

123. A make-up kit comprising a nail varnish comprising:
a first composition comprising at least one coloring matter in a cosmetically acceptable medium, and
a second composition comprising flat fibers in at least one cosmetically acceptable lipophilic continuous medium, wherein the flat fibers have a cross section having a longer length L1, and a shorter length L2, such that the ratio L1/L2 is greater than 4, wherein the flat fibers are of synthetic origin and have a cross-section shape chosen from ovoid and/or ellipsoid, and are in the form of unitary fibers, and
wherein the first composition does not comprise flat fibers as present in the second composition, and
wherein the first and second compositions are packaged in separate containers.

124. The make-up kit according to claim 123, wherein the flat fibers have a length L and a diameter D such that the ratio L/D ranges from 1.2 to 2,500.

125. The make-up kit according to claim 124 wherein the ratio L/D ranges from 1.5 to 500.

126. The make-up kit according to claim 125, wherein the ratio L/D ranges from 1.6 to 150.

127. The make-up kit according to claim 123, wherein the fibers have a diameter D, ranging from 2 nm to 500 μm, wherein D is the diameter of the circle in which the section of the fiber is inscribed.

128. The make-up kit according to claim 127, wherein the fibers have a diameter D, ranging from 100 nm to 100 μm.

129. The make-up kit according to claim 128, wherein the fibers have a diameter D, ranging from 1 μm to 70 μm.

130. The make-up kit according to claim 123, wherein the flat fibers have a length L ranging from 1 μm to 10 mm.

131. The make-up kit according to claim 130 wherein the flat fibers have a length L ranging from 0.1 mm to 5 mm.

132. The make-up kit according to claim 131, wherein the flat fibers have a length L ranging from 0.3 mm to 3.5 mm.

133. The make-up kit according to claim 123, wherein the ratio L1/L2 is greater than 7.

134. The make-up kit according to claim 123, wherein the ratio L1/L2 ranges from 4 to 15.

135. The make-up kit according to claim 123, wherein the ratio L1/L2 ranges from 6 to 12.

136. The make-up kit according to claim 135, wherein the ratio L1/L2 ranges from 7 to 10.

137. The make-up kit according to claim 123, wherein the flat fibers have a cross section shape chosen from rectangular, ovoid and ellipsoid shapes.

138. The make-up kit according to claim 123, wherein the flat fibers are in a form chosen from ribbons and tagliatelli form.

139. The make-up kit according to claim 123, wherein the flat fibers are twisted along the axis of the length L of the fibers.

140. The make-up kit according to claim 123, wherein the flat fibers have a titre ranging from 0.15 to 30 denier.

141. The make-up kit according to claim 140, wherein the flat fibers have a titre ranging from 0.18 to 18 denier.

142. The make-up kit according to claim 123, wherein the flat fibers comprise polymer fibers.

143. The make-up kit according to claim 123, wherein the flat fibers are chosen from rayon fibers, polyamide fibers, viscose fibers, acetate fibers, poly(p-phenylene-terephthalamide) fibers, acrylic polymer fibers, polyolefin fibers, polytetrafluoroethylene fibers, polyvinyl chloride fibers, polyvinylidene chloride fibers, polyvinylidene fluoride fibers, polyvinyl alcohol fibers, polyacrylonitrile fibers, polyurethane fibers, polyester fibers, and polycarbonate fibers.

144. The make-up kit according to claim 143, wherein the acetate fibers comprise rayon acetate fibers.

145. The make-up kit according to claim 143, wherein the acrylic polymer fibers are chosen from polymethyl methacrylate fibers and poly-2-hydroxyethyl methacrylate fibers.

146. The make-up kit according to claim 143, wherein the polyolefin fibers are chosen from polyethylene and polypropylene fibers.

147. The make-up kit according to claim 143, wherein the polyester fibers are chosen from polyethylene terephthalates and polyethylene naphthalates.

148. The make-up kit according to claim 143, wherein the flat fibers are chosen from polyester, acrylic polymer and polyamide fibers.

149. The make-up kit according to claim 142, wherein the flat fibers comprise a polymer chosen from polyethylene terephthalate, polyethylene naphthalate, polycarbonate, polymethyl methacrylate, nylon 6, nylon 6-6, nylon 6-12, nylon 11, and nylon 12.

150. The make-up kit according to claim 123, wherein the flat fibers comprise a multilayer structure of polymers having alternate layers of at least one first polymer and at least one second polymer.

151. The make-up kit according to claim 150, wherein the layers of polymers comprising the flat fibers are such that they allow the creation of a color effect by interferences of light rays, which diffract and diffuse differently according to the layers.

152. The make-up kit according to claim 150, wherein each layer of polymer is in a plane (P) parallel to the direction of the principal axis of the fiber, in the direction of its length L.

153. The make-up kit according to claim 150, wherein the multilayer fiber comprises at least 5 individual layers of polymer.

154. The make-up kit according to claim 153, wherein the multilayer fiber comprises individual layers of polymer ranging from 5 to 120 layers.

155. The make-up kit according to claim 154, wherein the multilayer fiber comprises at least 10 layers of polymer.

156. The make-up kit according to claim 155, wherein the multilayer fiber comprises individual layers of polymer ranging from 10 to 70 layers.

157. The make-up kit according to claim 156, wherein the multilayer fiber comprises individual layers of polymer ranging from 10 to 50 layers.

158. The make-up kit according to claim 150, wherein each layer of the at least one first and at least one second polymers have a thickness $d_1$, $d_2$, respectively, which may be identical or different, ranging from 0.02 μm to 0.3 μm.

159. The make-up kit according to claim 158, wherein the thicknesses, $d_1$, and $d_2$, which may be identical or different, range from 0.05 μm to 0.15 μm.

160. The make-up kit according to claim 150, wherein the polymers present in the fibers have a refractive index ranging from 1.30 to 1.82.

161. The make-up kit according to claim 160, wherein the polymers present in the fibers have a refractive index ranging from 1.35 to 1.75.

162. The make-up kit according to claim 150, wherein the at least one first and at least one second polymer layers have a refractive index $n_1$ and $n_2$, respectively, such that the ratio $n_1/n_2$ ranges from 1.1 to 1.4.

163. The make-up kit according to claim 150, wherein the flat fiber with a multilayer structure has a reflection spectrum such that the width at half height of the spectrum $\lambda_{L=1/2}$ ranges from 0 to 200 nm.

164. The make-up kit according claim 150, wherein the at least one first polymer comprises a polyester and the at least one second polymer comprises a polyamide.

165. The make-up kit according to claim 123, wherein the flat fibers are surface-treated or coated with a protective layer.

166. The make-up kit according to claim 165, wherein the protective layer comprises a polymer chosen from polyurethanes, polyethyl acrylates, and polyethyl methacrylates.

167. The make-up kit according to claim 123, wherein the flat fibers are present in the second composition in an amount ranging from 0.01% to 50% by weight, relative to the total weight of the second composition.

168. The make-up kit according to claim 167, wherein the flat fibers are present in the second composition in an amount ranging from 0.1% to 30% by weight, relative to the total weight of the second composition.

169. The make-up kit according to claim 168, wherein the flat fibers are present in the second composition in an amount ranging from 0.3% to 20% by weight, relative to the total weight of the second composition.

170. The make-up kit according claim 123, wherein the lipophilic continuous phase comprises at least one fatty substance chosen from oils, waxes, gums, pasty fatty substances, and lipophilic organic solvents.

171. The make-up kit according to claim 123, wherein at least one of the first and second composition comprises an aqueous, alcoholic or aqueous-alcoholic phase dispersed or emulsified in the lipophilic continuous phase.

172. The make-up kit according to claim 123, wherein at least one of the first and second composition comprises at least one film-forming polymer.

173. The make-up kit according to claim 172, wherein the at least one film-forming polymer is chosen from vinyl polymers, polyurethanes, polyesters, polyamides, and polyureas.

174. The make-up kit according to claim 172, wherein the at least one film-forming polymer is dissolved or dispersed in the form of particles in the lipophilic continuous phase.

175. The make-up kit according to claim 172, wherein the at least one film-forming polymer is present in the composition in a polymer dry matter amount ranging from 0.1% to 60% by weight, relative to the total weight of the composition.

176. The make-up kit according to claim 175, wherein the at least one film-forming polymer is present in the composition in a polymer dry matter amount ranging from 0.5% to 40% by weight, relative to the total weight of the composition.

177. The make-up kit according to claim 176, wherein the at least one film-forming polymer is present in the composition in a polymer dry matter amount ranging from 1% to 30% by weight, relative to the total weight of the composition.

178. The make-up kit according to claim 123, wherein the composition further comprises an additional particulate phase, which is present in an amount ranging from 0 to 48% by weight, relative to the total weight of the composition.

179. The make-up kit according to claim 178, wherein the additional particulate phase is present in an amount ranging from 0.01% to 30% by weight, relative to the total weight of the composition.

180. The make-up kit according to claim 179, wherein the additional particulate phase is present in an amount ranging from 0.02 to 20% by weight, relative to the total weight of the composition.

181. The make-up kit according to claim 178, wherein the particulate phase is chosen from pigments, pearlescent agents and fillers.

182. The make-up kit according to claim 123, wherein the second composition comprises a substantially translucent medium.

183. The make-up kit according to claim 123, wherein the first and second compositions are packaged in separate compartments.

184. A method of mechanically strengthening keratinous materials, comprising applying a nail varnish to a keratinous material, wherein said nail varnish comprises a lipophilic continuous phase, said phase containing flat fibers having a cross section having a longer length L1, and a shorter length L2, such that the ratio L1/L2 is greater than 4, wherein the flat fibers are of synthetic origin and have a cross-section shape chosen from ovoid and/or ellipsoid, and are in the form of unitary fibers.

185. A support to which a nail varnish has been applied, chosen from false nails, wherein the nail varnish applied to the support comprises in a cosmetically acceptable medium, at least one lipophilic continuous phase, said phase containing flat fibers having a cross section having a longer length L1, and a shorter length L2, such that the ratio L1/L2 is greater than 4, wherein the flat fibers are of synthetic origin and have a cross-section shape chosen from ovoid and/or ellipsoid, and are in the form of unitary fibers.

* * * * *